(12) United States Patent
Pedersen et al.

(10) Patent No.: US 11,019,434 B2
(45) Date of Patent: May 25, 2021

(54) HEARING PROTECTION DEVICE WITH RELIABILITY AND RELATED METHODS

(71) Applicant: GN Hearing A/S, Ballerup (DK)

(72) Inventors: Søren Christian Voigt Pedersen, Ballerup (DK); Peter Websdell, Ballerup (DK)

(73) Assignee: GN Hearing A/S, Ballerup (DK)

( * ) Notice: Subject to any disclaimer, the term of this patent is extended or adjusted under 35 U.S.C. 154(b) by 4 days.

(21) Appl. No.: 16/201,702

(22) Filed: Nov. 27, 2018

(65) Prior Publication Data

US 2019/0191254 A1    Jun. 20, 2019

(30) Foreign Application Priority Data

Dec. 20, 2017  (EP) .................................. 17209049

(51) Int. Cl.
  *H04R 25/00*  (2006.01)
  *H04R 1/10*  (2006.01)
  (Continued)

(52) U.S. Cl.
  CPC ............ *H04R 25/505* (2013.01); *A61F 11/08* (2013.01); *H04R 1/1016* (2013.01);
  (Continued)

(58) Field of Classification Search
  CPC .................... H04R 1/1016; H04R 1/1041; H04R 2460/01; H04R 2460/03; H04R 2460/15;
  (Continued)

(56) References Cited

U.S. PATENT DOCUMENTS 9,369,798 B1    6/2016  Alderson et al.
2008/0292126 A1*  11/2008  Sacha .................... H04R 25/02
                                                              381/330

(Continued)

FOREIGN PATENT DOCUMENTS

WO    WO 2008/138349 A2    11/2008
WO    WO 2008/138349 A3    11/2008

OTHER PUBLICATIONS

Extended European Search Report and search Opinion dated Jun. 11, 2018 for corresponding European patent application No. 17209049.0.

*Primary Examiner* — Matthew A Eason
(74) *Attorney, Agent, or Firm* — Vista IP Law Group, LLP

(57) ABSTRACT

A hearing protection device comprises a first earpiece comprising a first transducer for provision of a first ear canal input signal and a first receiver for provision of a first audio output signal based on a first ear canal output signal. The hearing protection device comprises a second earpiece comprising a second transducer for provision of a second ear canal input signal and a second receiver for provision of a second audio output signal based on a second ear canal output signal. The hearing protection device comprises a first mixer module, connected to the first earpiece and a controller module, for provision of a first output signal based on one or more first input signals. The hearing protection device comprises a second mixer module, connected to the second earpiece and the controller module, for provision of a second output signal based on one or more second input signals.

18 Claims, 5 Drawing Sheets

(51) Int. Cl.
*A61F 11/08* (2006.01)
*H04R 5/04* (2006.01)
*A61F 11/14* (2006.01)

(52) U.S. Cl.
CPC .......... *H04R 1/1083* (2013.01); *H04R 25/43* (2013.01); *H04R 25/70* (2013.01); *A61F 2011/145* (2013.01); *H04R 5/04* (2013.01); *H04R 2225/43* (2013.01); *H04R 2460/15* (2013.01)

(58) Field of Classification Search
CPC . H04R 2225/61; H04R 2410/05; H04R 29/00
See application file for complete search history.

(56) References Cited

U.S. PATENT DOCUMENTS

2011/0116643 A1* 5/2011 Tiscareno ............ H04R 1/1016
381/58
2012/0308020 A1 12/2012 Rung

* cited by examiner

HEARING PROTECTION DEVICE WITH RELIABILITY AND RELATED METHODS

RELATED APPLICATION DATA

This application claims priority to, and the benefit of, European Patent Application No. 17209049.0 filed on Dec. 20, 2017. The entire disclosure of the above application is expressly incorporated by reference herein.

FIELD

The present disclosure relates to a hearing protection device and related methods including a method of estimating a voice signal.

BACKGROUND

In noisy environments, it may be desirable for a user to protect his/her hearing while enabling the user to communicate with others via radio communication. Further, it may be challenging to deal leakage that occurs when one earpiece of the hearing protection system is not completely sealed or even worst has fallen out.

SUMMARY

Accordingly, there is a need for hearing protection devices and methods with improved reliability to detect leakage state and to provide a fall-back mechanism based on the detected leakage state.

A hearing protection device is disclosed. The hearing protection device comprises a first earpiece comprising a first transducer for provision of a first ear canal input signal and a first receiver for provision of a first audio output signal based on a first ear canal output signal. The hearing protection device comprises a second earpiece comprising a second transducer for provision of a second ear canal input signal and a second receiver for provision of a second audio output signal based on a second ear canal output signal. The hearing protection device comprises a first mixer module, connected to the first earpiece and a controller module, for provision of a first output signal based on one or more first input signals. The hearing protection device comprises a second mixer module, connected to the second earpiece and the controller module, for provision of a second output signal based on one or more second input signals. The hearing protection device comprises a controller module comprising a leakage detection module configured to determine a first leakage parameter, the first leakage parameter being indicative of a positioning of the first earpiece in a user ear canal, the controller module configured to control the first mixer module and/or the second mixer module based on the first leakage parameter.

Further, a method of operating a hearing device is provides. The method comprises obtaining a first input signal and a second input signal. The method comprises determining a first leakage parameter, the first leakage parameter being indicative of a positioning of the first earpiece in a user ear canal. The method comprises providing a control signal based on the first leakage parameter. The method comprises generating a first output signal based on any one or more of the control signal, the first input signal, and the second input signal. The method comprises generating a second output signal based on the control signal, the first input signal, and/or the second input signal.

It is an advantage of the hearing protection device with an improved reliability to detect leakage state and to provide a fall-back mechanism based on the detected leakage state. The hearing protection device disclosed herein is capable of automatically re-routing the input signals and/or of selecting the earpiece for optimally composing a clear transmission signal. A user being in a critical situation does not have to stop and re-insert an earpiece instantly to secure communication. The disclosed hearing protection device allows the user to wait for a better-suited moment to re-position the earpiece in the ear canal. In the meantime, critical communication is made reliable and can be maintained based on the disclosed method.

A hearing device includes: a first earpiece comprising a first transducer configured to provide a first ear canal input signal, and a first receiver configured to provide a first audio output signal based on a first ear canal output signal; a second earpiece comprising a second transducer configured to provide a second ear canal input signal, and a second receiver configured to provide a second audio output signal based on a second ear canal output signal; a controller module; a first mixer module connected to the first earpiece and to the controller module, the first mixer configured to provide a first output signal based on one or more first input signals; a second mixer module connected to the second earpiece and to the controller module, the second mixer configured to provide a second output signal based on one or more second input signals; and a controller module comprising a leakage detection module configured to determine a first leakage parameter, the first leakage parameter being indicative of a positioning of the first earpiece in a first ear canal of a user or a positioning of the second earpiece in a second ear canal of the user, the controller module configured to control the first mixer module and/or the second mixer module based on the first leakage parameter.

Optionally, the leakage detection module is configured to determine the first leakage parameter based on the one or more first input signals, and/or the one or more second input signals.

Optionally, the leakage detection module is configured to determine the first leakage parameter by determining a hearing protection estimate, wherein the hearing protection estimate comprises a first noise ratio between the first ear canal input signal and a first external input signal, and/or a second noise ratio between the second ear canal input signal and a second external input signal.

Optionally, the leakage detection module is configured to determine the first leakage parameter based on a first signal-to-noise ratio of the first ear canal input signal, and/or a second signal-to-noise ratio of the second ear canal input signal.

Optionally, the leakage detection module is configured to determine the first leakage parameter based on a first frequency response of the first mixer module and/or on a second frequency response of the second mixer module.

Optionally, the leakage detection module is configured to determine the first leakage parameter based on one or more sensor parameters obtained from one or more sensors.

Optionally, the one or more sensors comprise a capacitive sensor, and/or a proximity sensor.

Optionally, the leakage detection module is configured to determine the first leakage parameter by: determining a probability of the first earpiece is in a first position where the first earpiece does not seal the first ear canal, or in a second position where the first earpiece seals the first ear canal; or determining a probability of the second earpiece is in a first position where the second earpiece does not seal the second ear canal, or in a second position where the second earpiece seals the second ear canal.

Optionally, the first transducer comprises an ear canal microphone and/or a bone-conducting transducer.

Optionally, the one or more first input signals comprise one or more first external input signals received from a first source, and wherein the one or more second input signals comprise one or more second external input signals received from a second source.

Optionally, the controller module is configured to control the first mixer module and/or the second mixer module by selecting, as sink, the first earpiece and/or the second earpiece based on the first leakage parameter.

Optionally, the controller module is configured to apply: a first primary mixing scheme and a first secondary mixing scheme to generate the first ear canal output signal; and a second primary mixing scheme and a second secondary mixing scheme to generate the second ear canal output signal.

Optionally, the one or more first input signals comprise the first ear canal input signal obtained from the first transducer, and wherein the one or more second input signals comprise the second ear canal input signal obtained from the second transducer.

Optionally, the hearing device further includes a communication module coupled to the first mixer module and to the second mixer module.

Optionally, the controller module is configured to apply a first primary mixing scheme and a first secondary mixing scheme to cause the first mixer module to generate the first output signal, wherein the communication module is configured to obtain the first output signal.

Optionally, the hearing device is a hearing protection device.

A method of operating a hearing device, includes: obtaining a first input signal and a second input signal; determining a first leakage parameter, the first leakage parameter being indicative of a positioning of a first earpiece in a user's ear canal; providing a control signal based on the first leakage parameter; generating a first output signal based on any one or more of the control signal, the first input signal, and the second input signal; and generating a second output signal based on the control signal, the first input signal, and/or the second input signal.

Optionally, the first leakage parameter is determined based on the first input signal and/or the second input signal.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1A:
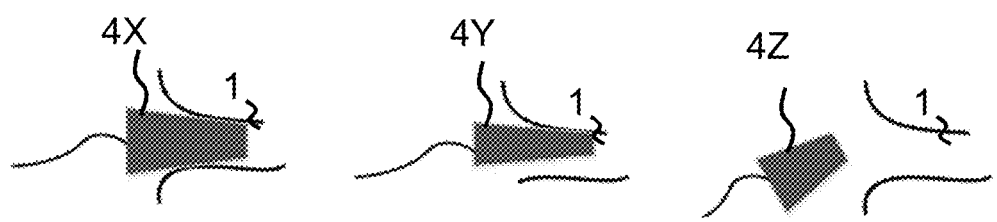
FIG. 1A schematically illustrates exemplary earpieces in various positions with respect to an ear canal of a user, according to this disclosure, FIG. 1B schematically illustrates an exemplary hearing protection device according to this disclosure, FIG. 2 schematically illustrates an exemplary first mixer module and an exemplary second mixer module for reception control according to the disclosure, FIG. 3 schematically illustrates an exemplary first mixer module and an exemplary second mixer module for transmission control according to the disclosure.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Tactical and life critical hearing devices use advanced communication devices utilizing several sensors and transducers. For example, for military use, the hearing device has to be hearing protecting certified. Hearing protection devices are often chosen for comfort and for minimizing the impact on the spatial cues needed for optimal situational awareness. Tactical communication devices are often controlled by a body worn unit interfacing to several (audio) communicating devices such two-way radios, intercom systems, intra-squad radios etc.

In order to separate the incoming audio and to ease the perception of the received audio, often the input signals are split into left and right earpiece. For example, when two radio sources are connected to the hearing protection device: radio 1 and radio 2. Radio 1 could be received in left earpiece and radio 2 could be received in the right earpiece. Another example could be to separate the incoming audio signal by means of Head Related Transfer Function, HRTF, in order to spatially separate the audio in order to optimize the user's ability to identify the radio source of the received audio.

However, the hearing protection device need to be robust and have a fail-safe and secure mechanism to remedy when one earpiece is not completely sealed or worst case fallen out. Such a situation could lead to audio commands being poorly received, or worst case not received at all. A similar problem occurs for transmissions of signals by the hearing protection devices. When the earpiece is used for composing the outgoing signal is poorly sealed (i.e. there is a leakage), or the earpiece has fallen out, a corrupted audio signal or even no signal can be captured and thereafter transmitted. In tactical communications, a security issue arises when these events occur.

The present disclosure attempts to detect such situations and provide a fail-safe and secure mechanism to remedy to poor seal and no seal of the ear canal by an earpiece of the hearing protection device.

The present disclosure provides a hearing protection device which aims at being robust against leakage and at providing a fall-back mechanism in case of leakage. Leakage can among other things be caused by wrongly inserted earpiece, incorrect choice of earpiece size (e.g. foam size), accidently drop out of earpiece due to e.g. movements. Leakage may be inexistent or present. When present, leakage may be total or partial. Total leakage relates to the earpiece has fallen out of the ear canal, and thereby is a not-inserted. Partial leakage relates to the earpiece partially sealing the ear canal and not fallen out of the ear canal. In the present disclosure, the inventors have found that leakage is detectable by utilizing one or more features leading into a decision based an algorithm that supports identifying leakage states ranging from no leakage (i.e. fully sealed ear canal, fully inserted earpiece), to partial leakage (i.e. partially sealed ear canal, partially inserted earpiece) and to total leakage (i.e. non-sealed ear canal, or non-inserted earpiece).

A hearing protecting device is disclosed. The hearing protection device comprises a first earpiece. The first earpiece comprises a first transducer for provision of a first ear canal input signal and a first receiver for provision of a first audio output signal based on a first ear canal output signal. An ear canal microphone is optionally configured to detect ear canal audio or sound via an ear canal opening in the earpiece housing. In one or more exemplary hearing protection devices, the hearing protection device comprises a first ear canal microphone and/or a second ear canal microphone for provision of respective first ear canal input signal and second ear canal input signal. The ear canal microphone may be arranged in an earpiece housing of an earpiece. For example, the first ear canal microphone is arranged in first earpiece housing of the first earpiece and the second ear canal microphone is arranged in second earpiece housing of the second earpiece. The first earpiece may be configured for a left ear of a user and the second earpiece may be configured for a right ear of a user or vice versa. The first receiver may be arranged in first earpiece housing of the first earpiece and/or the second ear canal microphone is arranged in second earpiece housing of the second earpiece. A receiver may provide the audio output signal via the ear canal opening in the ear canal portion or via an output port in the ear canal portion.

The hearing protection device comprises a second earpiece. The second earpiece comprises a second transducer for provision of a second ear canal input signal and a second receiver for provision of a second audio output signal based on a second ear canal output signal.

The first earpiece and the second earpiece may be seen as the right earpiece and the left earpiece respectively, and vice versa.

In one or more exemplary hearing protection devices, any of the first transducer and the second transducer comprises an ear canal microphone and/or a bone-conducting transducer.

The hearing protection device may comprise a set of ear canal microphones. The set of ear canal microphones may comprise one or more ear canal microphones. The set of ear canal microphones comprises a first ear canal microphone for provision of a first ear canal input signal and/or a second ear canal microphone for provision of a second ear canal input signal. The set of ear canal microphones may comprise N ear canal microphones for provision of N ear canal input signals, wherein N is an integer in the range from 1 to 10. In one or more exemplary hearing protection devices, the number N of ear canal microphones is two, three, four, five or more. The set of ear canal microphones may comprise a third ear canal microphone for provision of a third ear canal input signal.

The hearing protection device may comprise a processing device and one or more earpieces including the first earpiece and/or the second earpiece. The processing device is optionally wired to the first earpiece and the second earpiece. The processing device may be configured to be worn on the body, e.g. torso, arm or leg, of the user. The processing device may be configured to be attached to or integrated in a helmet.

An earpiece, such as first earpiece and/or second earpiece, comprises an earpiece housing. The earpiece housing may be configured for positioning in the ear of a user, such as in the concha and in the ear canal. The earpiece housing optionally comprises an ear canal portion and an outer ear portion. The ear canal portion extends along an ear canal axis, the ear canal portion having a first end. The first end of the ear canal portion points towards the eardrum of a user when the earpiece is inserted into the ear of a user. An ear canal opening may be arranged at the first end of the ear canal portion. The ear canal opening allows sounds to exit/enter the earpiece housing. A plurality of ear canal openings may be provided in the earpiece housing, e.g. to separate receiver sound and ear canal microphone sound. The ear canal opening(s) of the earpiece may each have a diameter in the range from 0.5 mm to 3 mm. The same or different diameters may be applied for different ear canal openings. The ear canal portion may have a length (measured along the ear canal axis) in the range from 2 mm to 20 mm. In one or more exemplary earpieces, the ear canal portion has a length in the range from 3 mm to 15 mm. Thereby, the ear canal wall of the user can be used for fixating the earpiece in the ear canal and/or the ear canal can be sealed near the tympanic membrane on the inner surface of the ear canal. An earpiece may be a hearing protector. Thus, earpiece, such as first earpiece and/or second earpiece, may comprise a protection element, e.g. for forming a seal between the ear canal wall and the ear canal portion (when inserted in the ear canal of the user). The protection element may be made of or comprise foamed polymer. The protection element may circumvent the ear canal portion. The protection element may have a length (extension along the ear canal axis) of at least 2 mm.

The hearing protection device may comprise a communication module for provision of one or more output signals (e.g. a first output signal for transmission, Tx) and one or more input signals (e.g. first received input signals, Rx).

In one or more exemplary hearing protection devices, the communication module may comprise an antenna for converting one or more wireless input signals, e.g. a first wireless input signal and/or a second wireless input signal, to a wireless output signal, e.g. a first wireless output signal. The wireless input signal(s) origin from external source(s), such as wireless transmitter, and/or a distributed microphone array associated with a wireless transmitter. The communication module may comprise a radio transceiver coupled to an antenna for converting the antenna output signal to a transceiver input signal. Wireless input signals from different external sources may be multiplexed in the radio transceiver to a transceiver input signal or provided as separate transceiver input signals on separate transceiver output terminals of the radio transceiver. The communication module may comprise a plurality of antennas and/or an antenna may be configured to be operate in one or a plurality of antenna modes. The transceiver input signal comprises a first transceiver input signal representative of the first wireless input signal from a first external source. The communication module may be configured to connect to an external radio device, which comprises a radio transceiver coupled to an antenna for converting the antenna output signal to a transceiver input signal.

In one or more exemplary hearing protection devices, the communication module is configured to receive one or more input signals via wired communication (e.g. via an intercom interface to an intercom system installed in a vehicle, such as tank or a helicopter).

The hearing protection device comprises a first mixer module, connected (e.g. operatively connected, e.g. coupled) to the first earpiece and a controller module, for provision of a first output signal based on one or more first input signals. A mixer module may comprise one or more filters, such as a static filter and/or an adaptive filter. A filter may be for example an Infinite Impulse Response (IIR) filter, and/or a Finite Impulse Response (FIR) filter. A filter may be of N'th order, e.g. where N is an integer in the range from 3 to 15, such as in the range from 4 to 10, for example 6 or 8. An IIR implementation of the filter(s) may be advantageous in that IIR filters are able to represent common features of the playback path (receiver, ear canal microphone, and/or acoustic properties of ear canal) using much fewer coefficients/lower order.

In one or more exemplary hearing protection devices, the first output signal comprises the first ear canal output signal and/or a first wireless input signal to the communication unit, so that communication module can transmit a first wireless output signal. In one or more exemplary hearing protection devices, the one or more first input signals comprise external input signals received from a first source, such as a first wireless input signal received via the communication module. In one or more exemplary hearing protection devices, the one or more first input signals comprise first ear canal input signals. In one or more exemplary hearing protection devices, a first mixer module is connected (e.g. operatively connected, e.g. coupled) to the first transducer and/or to the first ear canal microphone of the first earpiece. The first mixer and/or the second mixer may be arranged in processing device of the hearing protection device. A mixer may be configured to combine one or more input signals to provide one or more output signals. For example, the first mixer may be configured to combine one or more first input signals to provide one or more first output signals.

The hearing protection device comprises a second mixer module, connected (e.g. operatively connected, e.g. coupled) to the second earpiece and the controller module, for provision of a second output signal based on one or more second input signals. The second mixer module may be connected (e.g. operatively connected, e.g. coupled) to the first mixer module. For example, the second mixer may be configured to combine one or more second input signals to provide one or more second output signals. In one or more exemplary hearing protection devices, a second mixer module is connected (e.g. operatively connected, e.g. coupled) to the second transducer and/or to the second ear canal microphone of the first earpiece.

The hearing protection device comprises a controller module comprising a leakage detection module configured to determine a first leakage parameter. The first leakage parameter may be indicative of a positioning of the first earpiece in a user ear canal. The leakage refers to permeability of the sealing of the ear canal by an earpiece. Leakage relates to positioning of an earpiece in a user ear canal. In other words, there may be various leakage states ranging from a no leakage state (i.e. fully sealed ear canal, fully inserted earpiece), to a partial leakage state (i.e. partially sealed ear canal, partially inserted earpiece) and to a total leakage state (i.e. non-sealed ear canal, or non-inserted earpiece). A leakage parameter (such as the first leakage parameter) is indicative of a degree of leakage. A leakage parameter (such as the first leakage parameter) may be indicative of a leakage state. A leakage parameter may be in form of a leakage probability where a leakage probability of 0.0 corresponds to a total leakage state and a leakage probability of 1.0 corresponds to a no leakage state. In other words, the leakage may be characterized using a leakage parameter, which may be continuous (expressed by e.g. a probability between 0 and 1) or discrete (expressed by e.g. K leakage states, where K may be equal to 3 with (1) no leakage, (2) partial leakage, (3) total leakage).

In one or more exemplary hearing protection devices, to determine a first leakage parameter comprises to determine a probability of the first earpiece is in a first position where the earpiece does not seal the ear canal, or in a second position where the earpiece seals the ear canal. The first position may comprise a first primary position (e.g. indicative of a partial leakage state), a first secondary position (indicative of a total leakage state, e.g. the earpiece is not inserted, or dropped out). The second position is indicative of a no leakage state.

In other words, the controller module makes sure that received audio is always routed to an earpiece with the most favourable leakage state. Stated differently, if the leakage detection module detects leakage (total or partial) for any of the earpieces, the controller module controls the first mixer module and/or the second mixer module to make sure to re-direct the output signals to the other or best-sealed earpiece, or in other cases just slightly change a percentage split values between the earpieces.

The controller module is configured to control the first mixer module and/or the second mixer module based on the first leakage parameter.

The leakage detection module may be configured to determine a second leakage parameter indicative of a positioning of the second earpiece in a user ear canal. The controller module is configured to control the first mixer module and/or the second mixer module based on the second leakage parameter. The leakage parameter (e.g. first leakage parameter, and/or second leakage parameter) may be based on binaural input signals, such as first input signal and second input signal, such as first ear canal input signal and second ear canal input signal. The leakage parameter (e.g. first leakage parameter, and/or second leakage parameter) may be based on combination of binaural leakage parameters, such as right leakage parameter, and left leakage parameter.

The controller module may be configured to control the first mixer module and/or the second mixer module based on the first leakage parameter by determining one or more of a first primary mixing scheme, a first secondary mixing scheme, a second primary mixing scheme. A mixing scheme may comprise one or more mixing parameters, such as filter coefficients, and/or gain coefficients. Filter coefficients may be static. Filter coefficients may be adaptive. The filter coefficients may be selected to model electroacoustic properties of the receiver and the ear canal microphone, and/or to model acoustic properties of a sealed ear canal.

The controller module may comprise an own voice detector configured to detect if a user's own voice is present. The controller module may be configured to deactivate adaptation of the secondary filter coefficients in accordance with the own voice detector detecting presence of the user's own voice. The controller module may be configured to activate adaptive filter coefficients in the first and/or second mixer modules in accordance with the own voice detector detecting presence of the user's own voice. The first mixer module and/or the second mixer module may be configured to generate an own-voice signal.

The hearing protection device may comprise a (first) external microphone. An external microphone may be arranged in an earpiece housing of an earpiece and configured to pick up external or ambient sounds.

A hearing protection device may be a hearable or a hearing aid, wherein the processor is configured to compensate for a hearing loss of a user. The hearing protection device may be of the behind-the-ear (BTE) type, in-the-ear (ITE) type, in-the-canal (ITC) type, receiver-in-canal (RIC) type or receiver-in-the-ear (RITE) type. The hearing aid may be a binaural hearing aid.

The hearing protection device may comprise a first earpiece and a second earpiece, wherein the first earpiece and/or the second earpiece is an earpiece as disclosed herein.

In one or more exemplary hearing protection devices, the leakage detection module is configured to determine the first leakage parameter based on the one or more first input signals, and/or the one or more second input signals. For example, the leakage detection module may be configured to determine the first leakage parameter based on the one or more first input signals, and/or the one or more second input signals by determining a hearing protection estimate. The hearing protection estimate may comprise a first noise ratio between the first ear canal input signal and a first external input signal, and/or a second noise ratio between the second ear canal input signal and a second external input signal. In one or more exemplary hearing protection devices, the first noise ratio between the first ear canal input signal and a first external input signal is in the time domain. In one or more exemplary hearing protection devices, the first noise ratio between the first ear canal input signal and a first external input signal is in the frequency domain with K number of frequency bands. In one or more exemplary hearing protection devices, the second noise ratio between the second ear canal input signal and a second external input signal is in the time domain. In one or more exemplary hearing protection devices, the second noise ratio between the second ear canal input signal and a second external input signal is in the frequency domain with K number of frequency bands.

In one or more exemplary hearing protection devices, the leakage detection module is configured to determine the first leakage parameter based on a first signal-to-noise ratio of the first ear canal input signal, and/or a second signal-to-noise ratio of the second ear canal input signal. In other words, the leakage detection module is configured to determine the first leakage parameter based on a binaural signal-to-noise ratio, SNR, of the ear canal input signal (e.g. own voice signal). A good sealed fit would provide similar long-term SNR estimate of the ear canal input signal (e.g. the own-voice signal measured in the ear canal). A drop on one side may indicate leakage, as in the ear canal input signal (e.g. own voice pick up signal) is based on the ear canal input signal (e.g. occluded own voice signal). The leakage detection module may be configured to determine the first leakage parameter based on a variation of the first signal-to-noise ratio of the first ear canal input signal in time, such as a long-term variation. The leakage detection module may be configured to determine the first leakage parameter based on a variation of the second signal-to-noise ratio of the second ear canal input signal in time, such as a long-term variation.

In one or more exemplary hearing protection devices, the leakage detection module is configured to determine the first leakage parameter based on a first frequency response of the first mixer module and/or on a second frequency response of the second mixer module. For example, the first mixer module may comprise a first adaptive filter (e.g. for own-voice estimation), and the first frequency response of the first mixer may comprise a first frequency response of the first adaptive filter. For example, the second mixer module may comprise a second adaptive filter (e.g. for own-voice estimation), and the second frequency response of the second mixer module may comprise a second frequency response of the second adaptive filter. A combination of a static filter and an adaptive filter in a mixer module provides the ability to detect reduced low frequency gain in the adaptive filter, which leads to improved detection of a poor earpiece seal.

In one or more exemplary hearing protection devices, the leakage detection module is configured to determine the first leakage parameter based on one or more sensor parameters obtained from one or more sensors (e.g. in the first earpiece). In one or more exemplary hearing protection devices, the leakage detection module is configured to determine the second leakage parameter based on one or more sensor parameters obtained from one or more sensors (e.g. in the second earpiece). In one or more exemplary hearing protection devices, the one or more sensors comprise a capacitive sensor, and/or a proximity sensor. The one or more sensor parameters may comprise an indicator of leakage, such as an indicator of partial leakage state (e.g. ear canal not completely sealed) or an indicator of total leakage state (e.g. ear canal not sealed at all, earpiece dropped out of the ear canal).

In one or more exemplary hearing protection devices, the first one or more input signals comprise one or more first external input signals received from a first source. In one or more exemplary hearing protection devices, the one or more second input signals comprise one or more second external input signals received from a second source. The one or more first external input signals may be received from a first source via the communication module. The one or more second external input signals may be received from a second source via the communication module. In one or more exemplary hearing protection devices, the first mixer module is configured to provide a first output signal based on the one or more first external input signals received from a first source. In one or more exemplary hearing protection devices, the second mixer module is configured to provide a second output signal based on the one or more second external input signals received from a second source.

In one or more exemplary hearing protection devices, the controller module is configured to control the first mixer module and/or the second mixer module by selecting, as sink, one or more earpieces amongst the first earpiece and the second earpiece based on the first leakage parameter. In one or more exemplary hearing protection devices, the controller module is configured to control the first mixer module and/or the second mixer module by applying a first primary mixing scheme and a first secondary mixing scheme to generate the first ear canal output signal to the one or more selected earpieces (e.g. resulting in routing the first ear canal output signal to the one or more selected earpieces, and/or resulting in applying a head related transfer function the first ear canal output signal). In one or more exemplary hearing protection devices, the controller module is configured to control the first mixer module and/or the second mixer module by applying a second primary mixing scheme and a second secondary mixing scheme to generate the second ear canal output signal to the one or more selected earpieces (e.g. resulting in routing the second ear canal output signal to the one or more selected earpieces, and/or resulting in applying a head related transfer function to the second ear canal output signal). For example, a default configuration may be to route signal from two sources to each earpiece, utilizing head related transfer functions or simple percentage split values (e.g. first earpiece 0.2, second earpiece 0.8 or similar).

In one or more exemplary hearing protection devices, the first one or more input signals comprise one or more first ear canal input signals obtained from the first transducer. In one or more exemplary hearing protection devices, the one or more second input signals comprise one or more second ear canal input signals obtained from a second transducer. In one or more exemplary hearing protection devices, the first mixer module is configured to provide a first output signal based on the one or more first ear canal input signals obtained from a first transducer. In one or more exemplary hearing protection devices, the second mixer module is configured to provide a second output signal based on the one or more second ear canal input signals obtained from a second transducer.

In one or more exemplary hearing protection devices, the one or more first input signals comprise one or more first external input signals obtained via a first external microphone; and/or one or more second external input signals obtained via a second external microphone. In one or more exemplary hearing protection devices, the first mixer module is configured to provide a first output signal (e.g. for transmission) based on the one or more first external input signals obtained via the first external microphone. In one or more exemplary hearing protection devices, the second mixer module is configured to provide a second output signal (e.g. for transmission) based on the one or more second external input signals obtained via the second external microphone. The first output signal and/or the second output signal may be provided to the communication module for transmission.

In one or more exemplary hearing protection devices, the hearing protection device comprises a communication module for provision of a first output signal and the controller module is configured to control the first mixer module and/or the second mixer by selecting one or more first ear canal input signals based on the first leakage parameter and applying a first primary mixing scheme and a first secondary mixing schemes to generate the first output signal to the communication module. The controller module may be configured to control the first mixer module and/or the second mixer by selecting one or more second ear canal input signals based on a second leakage parameter and applying a second primary mixing scheme and a second secondary mixing schemes to generate the second output signal to the communication module e.g. for transmission. In other words, the controller module, would make sure that the transducer used to pick up the users' own voice is selected from the earpiece where leakage parameter is determined to be favorable. In some situations, the controller module prevents the hearing protection device from transmitting a signal obtained from an earpiece that has accidently falling out of the ear-canal. In other words, a secure hearing protection device for tactical and mission critical operations is hereby achieved.

The present disclosure provides a method of operating a hearing protecting device. The method comprises obtaining a first input signal and a second input signal. The method comprises determining a first leakage parameter, the first leakage parameter being indicative of a positioning of the first earpiece in a user ear canal. The method comprises providing a control signal based on the first leakage parameter. The method comprises generating a first output signal based on any one or more of the control signal, the first input signal, and the second input signal. The method comprises generating a second output signal based on the control signal, the first input signal, and/or the second input signal.

In one or more exemplary methods, determining a first leakage parameter comprises determining a first leakage parameter based on the first input signal and/or the second input signal.

The method or at least parts thereof may be performed by a hearing protection device as disclosed herein.

The figures are schematic and simplified for clarity. Throughout, the same reference numerals are used for identical or corresponding parts.

FIG. 1A schematically shows exemplary earpieces 4X, 4Y, 4Z in various positions with respect to an ear canal of a user. Earpiece 4X is inserted in the ear canal 1, so that the ear canal is sealed, which corresponds to a no leakage state according to this disclosure. Earpiece 4Y is inserted in the ear canal 1, so that the ear canal 1 is partially sealed, which corresponds to a partial leakage state according to this disclosure. Earpiece 4X is out of the ear canal 1 (e.g. has dropped out of the ear canal 1), so that the ear canal 1 is not sealed, which corresponds to a total leakage state according to this disclosure.

Figure 1B:
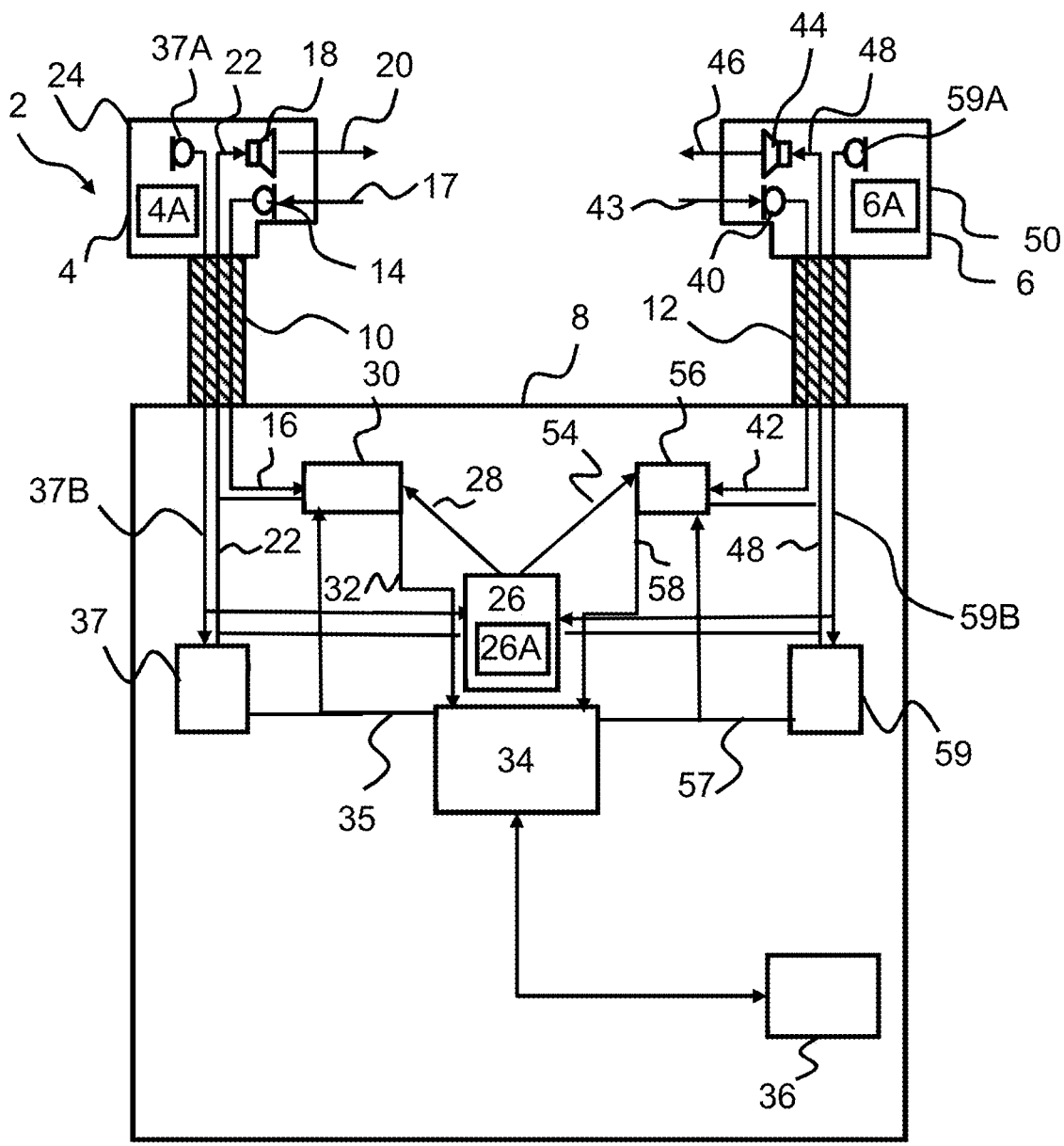

FIG. 1B schematically shows an exemplary hearing protection device 2 comprising a first earpiece 4, a second earpiece 6 and a processing device 8. The first earpiece 4 is connected to the processing device 8 with first cable 10 and the second earpiece 6 is connected to the processing device 8 with second cable 12.

The first earpiece 4 comprises a first transducer (e.g. first ear canal microphone 14) for provision of a first ear canal input signal (first ear canal input signal 16) based on first ear canal audio signal 17 detected by the first transducer (e.g. ear canal microphone 14). The first earpiece 4 comprises a receiver (first receiver 18) for provision of a first audio output signal (first audio output signal 20) based on a first ear canal output signal 22. The first transducer (e.g. first ear canal microphone 14) and the first receiver 18 are arranged in first earpiece housing 24 of the first earpiece 4.

The second earpiece 6 comprises a second transducer (e.g. second ear canal microphone 40) for provision of a second ear canal input signal (first ear canal input signal 42) based on second ear canal audio signal 43 detected by the second transducer (e.g. second ear canal microphone 40). The second earpiece 6 comprises a receiver (second receiver 44) for provision of a second audio output signal (second audio output signal 46) based on a second ear canal output signal 48. The second transducer (e.g. second ear canal microphone 40) and the second receiver 44 are arranged in second earpiece housing 50 of the second earpiece 6.

The hearing protection device 2 may comprise a communication module 34 and a first external microphone 37A. The communication module 34 may comprise a transceiver 36. The transceiver 36 may be coupled to an antenna for transmission and/or reception of signals. The antenna may be comprised in the hearing protection device. The antenna may be comprised in a radio device connectable to the hearing protection device.

In one or more exemplary hearing protection devices, the communication module 34 is configured to receive one or more input signals via wired communication (e.g. via an intercom interface). The transceiver 36 may be coupled to an intercom system, external to the hearing protection device, e.g. installed in a vehicle, such as tank or a helicopter.

The first external microphone 37A may be placed in the first earpiece 4. The hearing protection device 2 may comprise a first hearing protection processing module 37. The first hearing protection processing module 37 may be arranged in the processing device 8. The first hearing protection processing module 37 is connected to the first external microphone 37A for receiving first external input signal 37B from the first external microphone 37A and configured to provide first external output signal based on the first external input signal 37B. The first ear canal output signal 22 may be based on the first external output signal 37B and/or a first output signal 35 from the communication unit 34. The first ear canal output signal 22 may be a sum of the first external output signal 37B and the first output signal 35 from the communication unit 34.

The hearing protection device 2 optionally comprise a second hearing protection processing module 59 and second external microphone 59A. The second hearing protection processing module 59 is arranged in the processing device 8 and second external microphone 59A is arranged in the second earpiece housing 50. The second hearing protection processing module 59 is connected to the second external microphone 59A for receiving second external input signal 59B from the second external microphone 59A and configured to provide second external output signal based on the second external input signal 59B. The second ear canal output signal 48 may be based on the second external output signal 59B and/or a second output signal 57 from the communication unit 34. The second ear canal output signal 48 may be a sum of the second external output signal 59B and the second output signal 57 from the communication unit 34. The first hearing protection processing module 37 and the second hearing protection processing module 59 may be embedded in a single hearing protection processing module or embedded in the communication unit 34.

The hearing protection device 2 comprises a first mixer module (first mixer module 30) connected to the first transducer (first ear canal microphone 14) and the controller module 26. The first mixer module 30 is configured to provide a first output signal 32 based one or more first input signals (e.g. first ear canal input signal 16 and/or first external input signal 35, 37B). The first external input signal may be a signal 35 received via the communication module 34. The first external input signal may be a signal 37 obtained via the first external microphone 37A.

In one or more exemplary hearing protection devices, the one or more first input signals comprise one or more first external input signals 37B obtained via a first external microphone 37A; and/or one or more second external input signals 59B obtained via a second external microphone 59A. In one or more exemplary hearing protection devices, the first mixer module is configured to provide a first output signal 32 (e.g. for transmission) based on the one or more first external input signals 37B. In one or more exemplary hearing protection devices, the second mixer module is configured to provide a second output signal 34B (e.g. for transmission) based on the one or more second external input signals 59B.

In one or more hearing protection devices, the first mixer module 56 connected to the first ear canal microphone 14 may be configured to provide a first output signal 32 based on the first ear canal input signal 16 and the control signal 28.

The first output signal 32 may be fed to communication unit 34 for further processing and/or transmission via radio transceiver unit 36 configured to receive and/or transmit wireless signals; or via an external radio system.

The hearing protection device 2 comprises a second mixer module (second mixer module 56) connected to the second transducer (second ear canal microphone 40) and the controller module 26. The second mixer module 56 is configured to provide a second output signal 58 based one or more second input signals (e.g. second ear canal input signal 42 and/or second external input signal 59B, 57). The second external input signal may be a signal received via the communication module 34, or obtained via the second external microphone 59A.

In one or more hearing protection devices, the second mixer module 56 connected to the second ear canal microphone 40 for provision of a second output signal 58 based on the second ear canal input signal 42 and the control signal 54.

The second output signal 58 may be fed to communication unit 34 for further processing and/or transmission via radio transceiver unit 36 configured to receive and/or transmit wireless signals; or via an external radio system.

The hearing protection device 2 comprises a controller module 26 comprising a leakage detection module 26A configured to determine a first leakage parameter. The first leakage parameter may be indicative of a positioning of the first earpiece 4 in a user ear canal. The leakage detection module 26A may be configured to determine a second leakage parameter indicative of a positioning of the second earpiece 6 in a user ear canal. The controller module 26 is configured to control the first mixer 30 module and/or the second mixer module 56 based on the first leakage parameter and/or the second leakage parameter.

In one or more exemplary hearing protection devices, the leakage detection module 26A is configured to determine the first leakage parameter based on the one or more first input signals, and/or the one or more second input signals. For example, the leakage detection module may be configured to determine the first leakage parameter based on the one or more first input signals (e.g. first ear canal input signal 16 and/or first external input signal 37B, 35), and/or the one or more second input signals (e.g. second ear canal input signal 42 and/or second external input signal 59B, 57) by determining a hearing protection estimate. The hearing protection estimate may comprise a first noise ratio between the first ear canal input signal 16 and a first external input signal 37B, and/or a second noise ratio between the second ear canal input signal 42 and a second external input signal 59B. In one or more exemplary hearing protection devices, the first noise ratio between the first ear canal input signal 16 and a first external input signal 37B is in the time domain. In one or more exemplary hearing protection devices, the first noise ratio between the first ear canal input signal 16 and a first external input signal 37B is in the frequency domain with K number of frequency bands. The same may apply to the second noise ratio between the second ear canal input signal 42 and a second external input signal 59B.

In one or more exemplary hearing protection devices, the leakage detection module 26A is configured to determine the first leakage parameter based on a first signal-to-noise ratio of the first ear canal input signal 16, and/or a second signal-to-noise ratio of the second ear canal input signal 42. When it is determined by the leakage detection module 26A that the SNR estimate of the first ear canal input signal 16 (e.g. the own-voice signal measured in the ear canal) is substantially the same over a period of time that is sufficiently long, the leakage detection module determines a first leakage parameter to be indicative of a no leakage state (i.e. a good sealed fit, e.g. probability of leakage close to 1). A sufficiently long period of time may range from 2 to 10 seconds, such as 5-10 seconds. When it is determined by the leakage detection module 26A that the SNR estimate of the first ear canal input signal 16 includes a drop, the leakage detection module determines a first leakage parameter to be indicative of a partial or total leakage state (e.g. probability of leakage much less than 1). The leakage detection module 26A may be configured to determine the first leakage parameter based on a variation of the first signal-to-noise ratio of the first ear canal input signal 16 in time, such as a long-term variation. The leakage detection module 26A may be configured to determine the first leakage parameter based on a variation of the second signal-to-noise ratio of the second ear canal input signal 42 in time, such as a long-term variation.

In one or more exemplary hearing protection devices, the leakage detection module 26A is configured to determine the first leakage parameter based on a first frequency response of the first mixer module 30 and/or on a second frequency response of the second mixer module 56. For example, the first mixer module 30 may comprise a first adaptive filter (e.g. for own-voice estimation), and the first frequency response of the first mixer module 30 may comprise a first frequency response of the first adaptive filter. For example, the second mixer module 56 may comprise a second adaptive filter (e.g. for own-voice estimation), and the second frequency response of the second mixer module 56 may comprise a second frequency response of the second adaptive filter.

In one or more exemplary hearing protection devices, the leakage detection module 26A is configured to determine the first leakage parameter based on one or more sensor parameters obtained from one or more sensors 4A (placed in the first earpiece housing 24 of the first earpiece 4). In one or more exemplary hearing protection devices, the one or more sensors 4A comprise a capacitive sensor, and/or a proximity sensor. In one or more exemplary hearing protection devices, the leakage detection module 26A is configured to determine the second leakage parameter based on one or more sensor parameters obtained from one or more sensors 6A (placed in the second earpiece housing 50 of the second earpiece 6). In one or more exemplary hearing protection devices, the one or more sensors 6A comprise a capacitive sensor, and/or a proximity sensor. The one or more sensor parameters may comprise an indicator of leakage, such as an indicator of partial leakage state (e.g. ear canal not completely sealed) or an indicator of total leakage state (e.g. ear canal not sealed at all, earpiece dropped out of the ear canal).

In one or more exemplary hearing protection devices, the first one or more input signals comprise one or more first external input signals (e.g. signal 35 from the communication module 34) received from a first source (not shown). In one or more exemplary hearing protection devices, the one or more second input signals comprise one or more second external input signals received from a second source (e.g. signal 57 from the communication module 34). The one or more first external input signals may be received from a first source via the communication module.

In one or more exemplary hearing protection devices, the controller module 26 is configured to control the first mixer module 30 and/or the second mixer module 56 by selecting, as sink, one or more earpieces amongst the first earpiece 4 and the second earpiece 6 based on the first leakage parameter. In one or more exemplary hearing protection devices, the controller module 26 is configured to control the first mixer module 30 and/or the second mixer module 56 by applying a first primary mixing scheme and a first secondary mixing scheme to generate the first ear canal output signal 22 to the one or more selected earpieces (e.g. resulting in routing the first ear canal output signal 22 to the one or more selected earpieces, and/or resulting in applying a head related transfer function or filters to generate the first ear canal output signal 22). In one or more exemplary hearing protection devices, the controller module 26 is configured to control the first mixer module 30 and/or the second mixer module 56 by applying a second primary mixing scheme and a second secondary mixing scheme to generate the second ear canal output signal 48 to the one or more selected earpieces (e.g. resulting in routing the second ear canal output signal 48 to the one or more selected earpieces, and/or resulting in applying a head related transfer function to the second ear canal output signal). For example, the controller module 26 is configured to control the first mixer module 30 and the second mixer module 56 by applying a first primary mixing scheme and a first secondary mixing scheme to generate the first ear canal output signal 22 to the first earpiece 4, such as to the first receiver 18, and/or to the second earpiece 6, such as to the second receiver 44.

In one or more exemplary hearing protection devices, the controller module 26 is configured to control the first mixer module 30 and/or the second mixer module 56 by selecting one or more first ear canal input signals 16 based on the first leakage parameter and applying a first primary mixing scheme and a first secondary mixing schemes to generate the first output signal 32 to the communication module. The controller module 26 may be configured to control the first mixer module 30 and/or the second mixer module 56 by selecting one or more second ear canal input signals 42 based on a second leakage parameter and applying a second primary mixing scheme and a second secondary mixing schemes to generate the second output signal 58 to the communication module e.g. for transmission.

Figure 2:
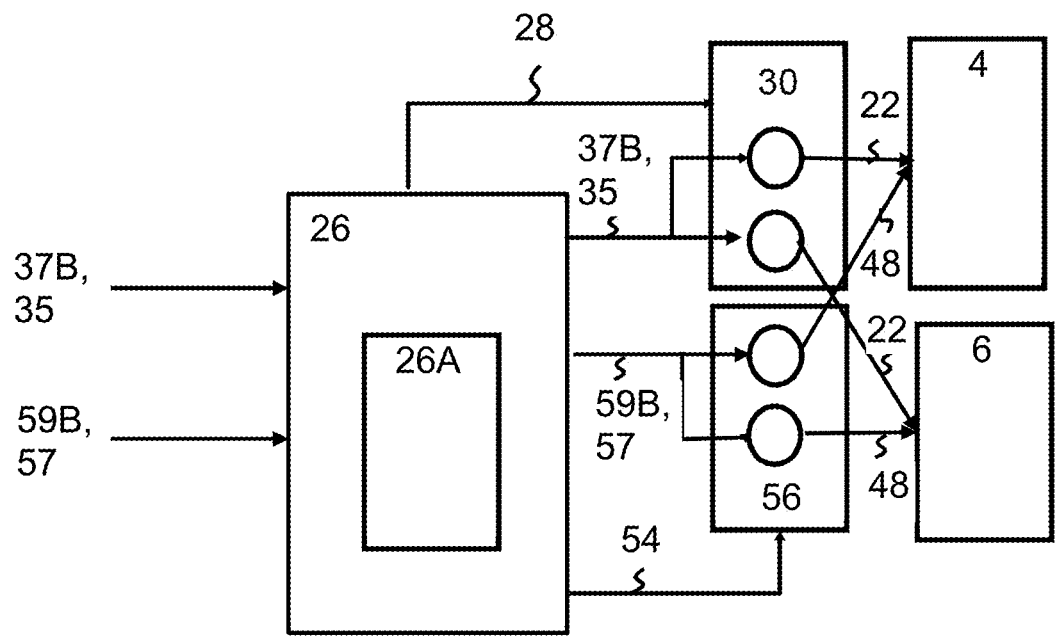

FIG. 2 is a block diagram 200 illustrating schematically an exemplary controller module 26, an exemplary first mixer module 30, an exemplary second mixer module 56 according to the disclosure. The first mixer module 30 is connected to a first earpiece 4 (such as the left earpiece) and to a second earpiece 6 (such as the right earpiece). The second mixer module 56 is connected to a first earpiece 4 and to a second earpiece 6. The controller module 26 comprises a leakage detection module 26A. The controller module 26 is configured to obtain as input: a first external input signal 37B from a first external microphone (not shown), and/or an input signal 35 from the communication module (not shown) received from a first source (not shown). The controller module 26 is configured to obtain as input: a second external input signal 59B from the second external microphone (not shown), or an input signal 57 from the communication module (not shown) from a second source (not shown). The controller module 26 is configured to control the first mixer module 30 and the second mixer module 56 by selecting, as sink for the first ear canal output signal 22, the first earpiece 4 and the second earpiece 6 based on the first leakage parameter, and by providing control signal 28 indicative of which earpiece is selected and of which mixing scheme to apply in the first mixer module 30. The first mixer module 30 is configured to generate the first ear canal output signal 22 based on the control signal 28, and any one or more of the first external input signal 37B and the input signal 35, by applying a first primary mixing scheme and a first secondary mixing scheme to any one or more of the first external input signal 37B and the input signal 35 to generate the first ear canal output signal 22. The first mixer module 30 is configured to provide the first ear canal output signal 22 to the one or more selected earpieces (e.g. the first earpiece 4 (such as the left earpiece) and/or the second earpiece 6 (such as the right earpiece)) based on the indication given in control signal 28. This way, the first ear canal output signal 22 is routed to the first earpiece 4 and/or the second earpiece 6 depending on the first leakage parameter which is indicative of leakage state at the first earpiece 4 and/or the second leakage parameter which is indicative of leakage state at the second earpiece 6.

Applying a first primary mixing scheme and a first secondary mixing scheme to any one or more of the first external input signal 37B and the input signal 35 may comprise applying a head related transfer function to signals 37B, 35 to generate the first ear canal output signal 22.

The controller module 26 is configured to control the first mixer module 30 and the second mixer module 56 by selecting, as sink for the second ear canal output signal 48, the first earpiece 4 and the second earpiece 6 based on the first leakage parameter, and by providing control signal 54 indicative of which earpiece is selected and of which mixing scheme to apply in the second mixer module 56. The second mixer module 56 is configured to generate the second ear canal output signal 48 based on the control signal 28, and any one or more of the second external input signal 59B and the input signal 57, by applying a second primary mixing scheme and a second secondary mixing scheme to any one or more of the second external input signal 59B and the input signal 57 to generate the second ear canal output signal 48. The second mixer module 56 is configured to provide the second ear canal output signal 48 to the one or more selected earpieces (e.g. the first earpiece 4 (such as the left earpiece) and/or the second earpiece 6 (such as the right earpiece)) based on the indication given in control signal 54. This way, the second ear canal output signal 48 is routed to the first earpiece 4 and/or the second earpiece 6 depending on the first leakage parameter which is indicative of leakage state at the first earpiece 4 and/or the second leakage parameter which is indicative of leakage state at the second earpiece 6.

Applying a first primary mixing scheme and a first secondary mixing scheme to any one or more of the second external input signal 59B and the input signal 57 may comprise applying a head related transfer function to signals 59B, 57 to generate the second ear canal output signal 48.

Figure 3:
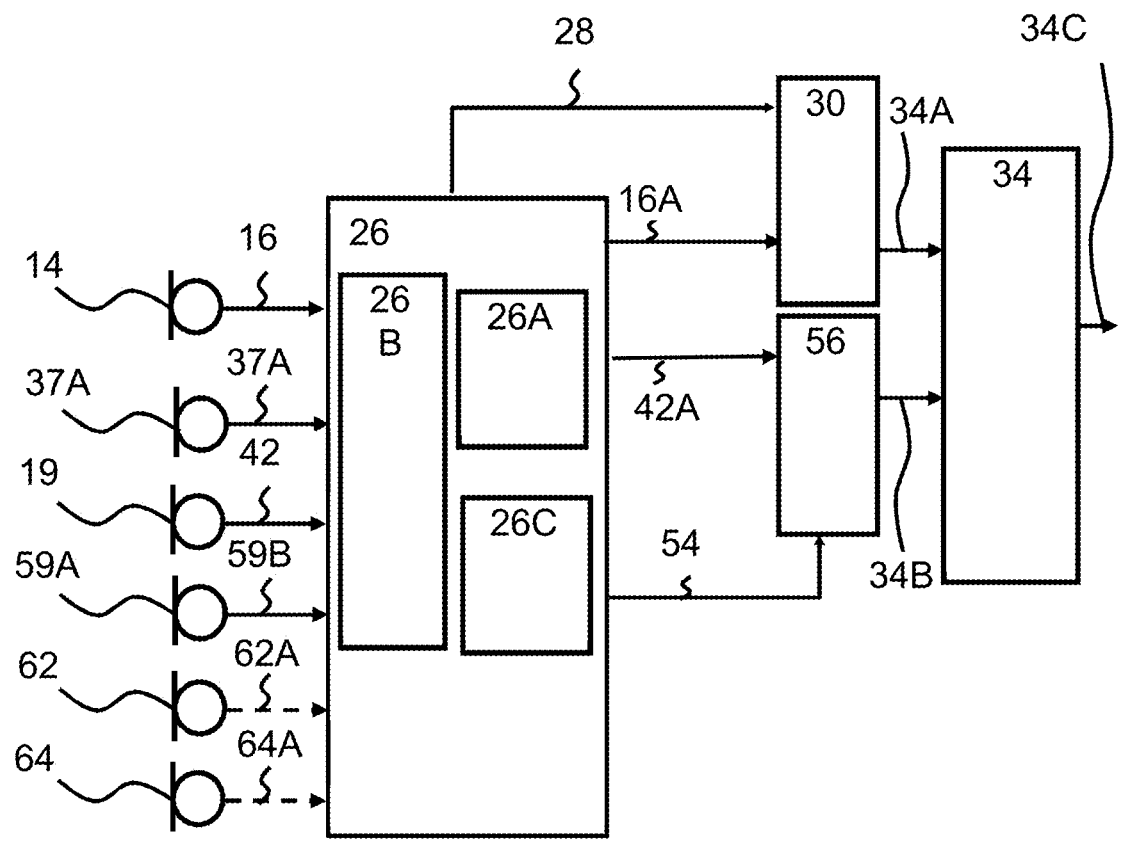

FIG. 3 is a block diagram 200 illustrating schematically an exemplary controller module 26, an exemplary first mixer module 30, an exemplary second mixer module 56 according to the disclosure. The first mixer module 30 is connected to a communication module 34. The controller module 26 is connected to a first ear canal microphone 14, and a first external microphone 37A (e.g. an omnidirectional ambient microphone). Optionally The controller module 26 is connected to a bone conduction microphone 62, and optionally a boom microphone 64.

The controller module 26 comprises a leakage detection module 26A, a multiplexer module 26B, and optionally a voice detection module 26C (e.g. an own-voice detection module). The leakage detection module 26A is configured to operate according to this disclosure and detect leakage. The multiplexer module 26B may be configured to multiplex (or map) M microphone input signals from N microphones to generate L multiplexed input signals. The multiplexer module 26B may be configured to multiplex (or map) a first ear canal input signal 16, a first external input signal 37A, optionally a bone conduction input signal 62A, and optionally a boom input signal 64A to generate multiplexed input signals. The multiplexed input signals may be fed to the voice detection module 26C. The voice detection module 26C is configured to process the multiplexed input signals into input signals 16A, 42A to the first mixer module 30 and to the second mixer module 56.

The first mixer module 30 is configured to provide a first output signal 34A based on the one or more first ear canal input signals 16A obtained from a first ear canal microphone 14. In one or more exemplary hearing protection devices, the second mixer module 56 is configured to provide a second output signal 34B based on the one or more second ear canal input signals 42 obtained from a second ear canal microphone 40.

The communication module 34 is configured for provision of a first output signal 34C based on first output signal 34A and second output signal 34B. The controller module 26 is configured to control the first mixer module 30 and/or the second mixer module 56 by selecting one or more first ear canal input signals 16, 16A based on the first leakage parameter determined by the leakage detection module 26A. The controller module 26 is configured to instruct the first mixer module 30 to apply a first primary mixing scheme and a first secondary mixing schemes to generate the first output signal 34A to the communication module 34. The controller module 26 is configured to control the first mixer module 30 and/or the second mixer module 56 by selecting one or more second ear canal input signals 42 based on a second leakage parameter. The controller module 26 is configured to instruct the second mixer module 56 to applying a second primary mixing scheme and a second secondary mixing schemes to generate the second output signal 34B to the communication module 34 e.g. for transmission.

Figure 4:
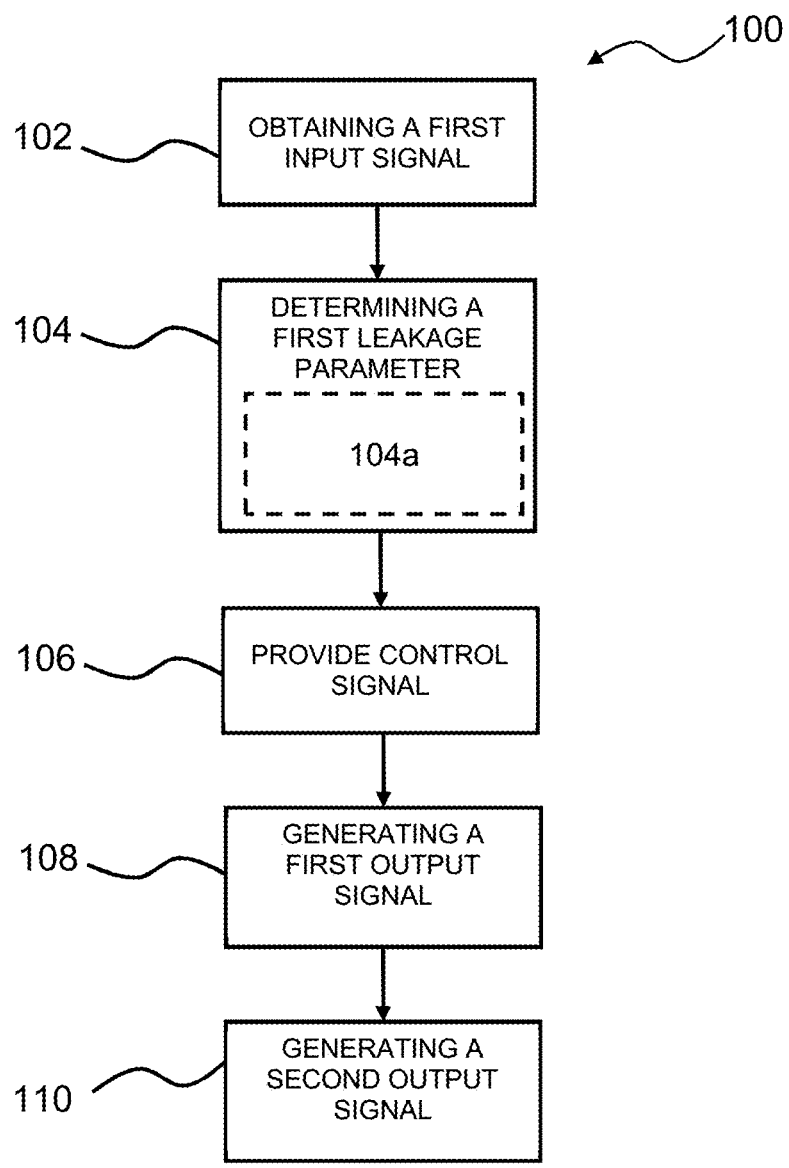
FIG. 4 is a flow diagram of an exemplary method according to the disclosure.

FIG. 4 shows a flow diagram of an exemplary method 100 of operating a hearing protection device according to the disclosure. The method 100 comprises obtaining 102 a first input signal and a second input signal. The method comprises determining 104 a first leakage parameter, the first leakage parameter being indicative of a positioning of the first earpiece in a user ear canal. The method comprises providing 106 a control signal based on the first leakage parameter. The method comprises generating 108 a first output signal based on any one or more of the control signal, the first input signal, and the second input signal. The method comprises generating 110 a second output signal based on the control signal, the first input signal, and/or the second input signal.

In one or more exemplary methods, determining 104 a first leakage parameter comprises determining 104a a first leakage parameter based on the first input signal and/or the second input signal.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 1 ear canal
2, 2A hearing protection system
4 first earpiece
4X, 4Y, 4Z earpiece
6 second earpiece
8 processing device
10 first cable
12 second cable
14 first ear canal microphone
16 first ear canal input signal
17 first ear canal audio signal
18 first receiver
20 first audio output signal
22 first ear canal output signal
24 first earpiece housing
26 controller module
28 control signal
30 first mixer
32 first output signal
34 communication unit
34A first output signal
34B second output signal
34C first output signal from communication unit
35 first output signal from communication unit
36 radio transceiver unit
37 first hearing protection processing module
37A first external microphone
37B first external input signal
40 second ear canal microphone
42 second ear canal input signal
43 second ear canal audio signal
44 second receiver
46 second audio output signal
48 second ear canal output signal
50 second earpiece housing
54 control signal
56 second mixer
57 second output signal from communication unit
58 second output signal
59 second hearing protection processing module
59A second external microphone
59B second external input signal
62 bone conduction microphone
64 boom microphone
100 method of operating a hearing protecting device
102 obtaining a first input signal and a second input signal
104 determining a first leakage parameter, the first leakage parameter being indicative of a positioning of the first earpiece in a user ear canal
104a determining a first leakage parameter based on the first input signal and/or the second input signal
106 providing a control signal based on the first leakage parameter
108 generating a first output signal based on any one or more of the control signal, the first input signal, and the second input signal
110 generating a second output signal based on the control signal, the first input signal, and/or the second input signal

The invention claimed is:

1. A hearing device comprising:
a first earpiece comprising a first transducer configured to provide a first ear canal input signal, and a first receiver configured to provide a first audio output signal based on a first ear canal output signal;
a second earpiece comprising a second transducer configured to provide a second ear canal input signal, and a second receiver configured to provide a second audio output signal based on a second ear canal output signal;
a controller module;
a first mixer module connected to the first earpiece and to the controller module, wherein the first mixer module is coupled upstream with respect to the first receiver, and is configured to perform first signal mixing, the first mixer configured to provide a first output signal based on one or more first input signals, wherein the first output signal comprises a first combined signal, and wherein the first mixer is configured to perform the first signal mixing by performing first signal-combining to provide the first combined signal; and
a second mixer module connected to the second earpiece and to the controller module, wherein the second mixer module is coupled upstream with respect to the second receiver, and is configured to perform second signal mixing, the second mixer configured to provide a second output signal based on one or more second input signals, wherein the second output signal comprises a first combined signal, and wherein the second mixer is configured to perform the second signal mixing by performing second signal-combining to provide the second combined signal;
wherein the controller module comprises a leakage detection module configured to determine a first leakage parameter, the first leakage parameter being indicative of a positioning of the first earpiece in a first ear canal of a user or a positioning of the second earpiece in a second ear canal of the user, the controller module configured to control the first mixer module and/or the second mixer module based on the first leakage parameter.

2. The hearing device according to claim 1, wherein the leakage detection module is configured to determine the first leakage parameter based on the one or more first input signals, and/or the one or more second input signals.

3. The hearing device according to claim 1, wherein the leakage detection module is configured to determine the first leakage parameter by determining a hearing protection estimate, wherein the hearing protection estimate comprises a first noise ratio between the first ear canal input signal and a first external input signal, and/or a second noise ratio between the second ear canal input signal and a second external input signal.

4. The hearing device according to claim 1, wherein the leakage detection module is configured to determine the first leakage parameter based on a first signal-to-noise ratio of the first ear canal input signal, and/or a second signal-to-noise ratio of the second ear canal input signal.

5. The hearing device according to claim 1, wherein the leakage detection module is configured to determine the first leakage parameter based on a first frequency response of the first mixer module and/or on a second frequency response of the second mixer module.

6. The hearing device according to claim 1, wherein the leakage detection module is configured to determine the first leakage parameter based on one or more sensor parameters obtained from one or more sensors.

7. The hearing device according to claim 6, wherein the one or more sensors comprise a capacitive sensor, and/or a proximity sensor.

8. The hearing device according to claim 1, wherein the leakage detection module is configured to determine the first leakage parameter by:

determining a probability of the first earpiece is in a first position where the first earpiece does not seal the first ear canal, or in a second position where the first earpiece seals the first ear canal; or determining a probability of the second earpiece is in a first position where the second earpiece does not seal the second ear canal, or in a second position where the second earpiece seals the second ear canal.

9. The hearing device according to claim 1, wherein the first transducer comprises an ear canal microphone and/or a bone-conducting transducer.

10. The hearing device according to claim 1, wherein the one or more first input signals comprise one or more first external input signals received from a first source, and wherein the one or more second input signals comprise one or more second external input signals received from a second source.

11. The hearing device according to claim 1, wherein the controller module is configured to control the first mixer module and/or the second mixer module by selecting, as sink, the first earpiece and/or the second earpiece based on the first leakage parameter.

12. The hearing device according to claim 1, wherein the controller module is configured to apply:
 a first primary mixing scheme and a first secondary mixing scheme to generate the first ear canal output signal; and
 a second primary mixing scheme and a second secondary mixing scheme to generate the second ear canal output signal.

13. The hearing device according to claim 1, wherein the one or more first input signals comprise the first ear canal input signal obtained from the first transducer, and wherein the one or more second input signals comprise the second ear canal input signal obtained from the second transducer.

14. The hearing device according to claim 1, further comprising a communication module coupled to the first mixer module and to the second mixer module.

15. The hearing device according to claim 14, wherein the controller module is configured to apply a first primary mixing scheme and a first secondary mixing scheme to cause the first mixer module to generate the first output signal, wherein the communication module is configured to obtain the first output signal.

16. The hearing device according to claim 1, wherein hearing device is a hearing protection device.

17. A method of operating a hearing device, the method comprising:
 obtaining a first input signal and a second input signal;
 determining a first leakage parameter, the first leakage parameter being indicative of a positioning of a first earpiece in a user's ear canal;
 providing a control signal based on the first leakage parameter;
 generating a first output signal based on any one or more of the control signal, the first input signal, and the second input signal, wherein the first output signal is generated by a first mixer that is configured to perform first signal-combining to provide a first combined signal; and
 generating a second output signal based on the control signal, the first input signal, and/or the second input signal, wherein the second output signal is generated by a second mixer that is configured to perform second signal-combining to provide a second combined signal.

18. The method according to claim 17, wherein the first leakage parameter is determined based on the first input signal and/or the second input signal.

\* \* \* \* \*